United States Patent
Kershman et al.

(10) Patent No.: US 6,340,471 B1
(45) Date of Patent: Jan. 22, 2002

(54) METHOD FOR PREPARING SOLID DELIVERY SYSTEM FOR ENCAPSULATED AND NON-ENCAPSULATED PHARMACEUTICALS

(76) Inventors: Alvin Kershman, 5032 Oakbluff Dr., Paradise Valley, MO (US) 63049; Jeff L. Shear, 1421 Wildhorse Parkway Dr., Chesterfield, MO (US) 63005

( * ) Notice: Subject to any disclaimer, the term of this patent is extended or adjusted under 35 U.S.C. 154(b) by 0 days.

(21) Appl. No.: 09/476,483

(22) Filed: Dec. 30, 1999

(51) Int. Cl.$^7$ .............................. A61K 9/16; A61K 9/20
(52) U.S. Cl. ...................... 424/439; 424/441; 424/464; 424/465; 424/490; 424/498; 514/783; 514/778; 514/784; 514/951
(58) Field of Search ................................. 424/400, 451, 424/455, 464, 484, 489, 490, 493, 494, 495, 502, 439, 441, 498, 465

(56) References Cited

U.S. PATENT DOCUMENTS

| | | | |
|---|---|---|---|
| 4,555,399 A | * 11/1985 | Hsiao | |
| 4,581,381 A | 4/1986 | Morris et al. | ................ 514/819 |
| 4,684,516 A | * 8/1987 | Bhutani | |
| 4,749,575 A | 6/1988 | Rotman | ....................... 424/441 |
| 4,797,288 A | * 1/1989 | Sharma et al. | |
| 4,842,863 A | * 6/1989 | Nishimura et al. | |
| 4,880,634 A | * 11/1989 | Speiser | |
| 4,888,178 A | * 12/1989 | Rotini et al. | |
| 5,525,352 A | 6/1996 | Kontos et al. | ............... 424/440 |

FOREIGN PATENT DOCUMENTS

| | | |
|---|---|---|
| WO | 97/34496 | 9/1997 |
| WO | 99/47122 | 9/1999 |

OTHER PUBLICATIONS

Stedman's Medical Dictionary (Medical Economics Company, Inc. 2001), definition of "homogeneous."*
Stedman's Medical Dictionary (Medical Economics Company, Inc. 2001), definition of "suspension."*

* cited by examiner

*Primary Examiner*—James M. Spear
(74) *Attorney, Agent, or Firm*—Linda L. Lewis; Glenn K. Robbins, II; Greensfelder, Hemker & Gale, P.C.

(57) ABSTRACT

A method for producing a delivery system for transporting pharmaceuticals and other ingredients in a chewable and palatable form is provided. The delivery system comprises a lipid source in which drug actives are homogeneously suspended to form a high solids suspension which can be solidified and molded into an oral dosage form. The lipid source provides an external phase comprising the carrier for the suspension and also provides a hydrophobic film which continuously coats the hydrophilic drug actives and other ingredients. The suspension exhibits pseudoplastic and thixotropic properties which enable it to suspend a large volume of particles relative to the lipid source. The drug particles may be pre-encapsulated before mixing in with the suspension, which provides taste-masking and controlled release qualities to the products formed from the delivery system.

14 Claims, No Drawings

METHOD FOR PREPARING SOLID DELIVERY SYSTEM FOR ENCAPSULATED AND NON-ENCAPSULATED PHARMACEUTICALS

BACKGROUND OF THE INVENTION

This invention relates to a method for producing an oral drug delivery system that can be provided in a chewable oral dosage form for both human and animal use.

It is always a challenge to administer pharmaceuticals to animals, not only in getting the animal to accept the drug, but also in administering the correct dosage. Clearly, animals are often unwilling to accept the more direct and invasive means of delivery, such as hypodermic needle injections, forced oral delivery of large boluses, or even topical applications of salves. These methods usually are met with limited cooperation by the animal. During administration of a drug, the relative uncooperativeness of the animal affects the degree to which the complete dosage is able to be delivered. Ideally, a drug delivery system should be one in which the animal is unaware that it is even being administered a drug. Some methods, accordingly, employ a drug supplement which can be added to an animal's food so that it will voluntarily, albeit unknowingly, ingest the drug along with the food. However, animals generally have a keen sense of taste and smell and can often detect the rather strong taste and smell of most pharmaceuticals. Animals are reluctant to consume anything that has a taste foreign to their standard diet. Thus, drug-supplemented food is frequently ineffective for delivery of drugs to animals as the animal may regurgitate, spit out, or even refuse to eat the food.

To address the problem of animals' high sensitivity to the taste of the pharmaceuticals, various taste masking methods have been employed in the prior art. One method is to add flavorings to help offset the taste of the drug chemical. This, however, does not remove the drug taste, per se, but rather, creates a relative diminished taste; the drug taste is nonetheless still present. To help suppress the taste of the drug, microencapsulation of the drug active may be used which places a coating around minute drug particles to seal off the taste emanating from the drug. The microencapsulating coating, however, is relatively fragile and, if disrupted, becomes ineffective in containing the taste of the drug. The relative fragility of the microencapsulation therefore leads to problems in preparing delivery vehicles for the drug. Tablets are a common source for delivering drugs. However, the compression inherent in the tableting process will disrupt the protective coating of the encapsulation, rendering its taste masking properties ineffective. While excessive microencapsulation coating can be employed to compensate for the damage attendant with tableting, such a process would significantly increase the cost of manufacturing the drug tablet. The microencapsulated drug actives might alternately be dry-filled into a gelatin capsule; however, this is also a costly procedure in that there is an inefficient use of space within the gelatin capsule, thus decreasing the amount of active drug present within the dose. Further, the gelatin capsule does not lend itself to being a potential chewable product, which is a desirable characteristic for getting the animal to ingest the drug.

Another concern in producing drug delivery systems is for the drug to have certain controlled release properties such as immediate release and sustained release for controlling the concentration and rate of drug available for action on the animal's physiological system. Drugs can be targeted for release in terms of time (i.e., rapid or slow) and/or location (i.e., mouth or intestinal tract). Controlled release characteristics are imparted to drug actives by forming them into a pellet for sustained release or in tiny particles for immediate release. The rate of release is affected by the degree of surface area exposed in relation to the mass of the drug active particle; the rate of release is greatest when the particles have a large surface area in relation to their overall mass. Controlled release characteristics are adversely and unpredictably affected by compressing the drug actives into a tablet, as it distorts the actives' surface area to mass ratio. There have been attempts to solve the tableting problem relative to sustained release pellets by complicated formulations that take into account the breakage of pellets that will occur during the tableting process. However, this breakage issue is not reproducible. Therefore, many batches produced by this method will likely be rejected for not meeting final release specifications. Tablets can, however, be designed in themselves to have controlled release properties without the need for adding preprocessed pellets. It is also possible to produce tablets that have taste masking properties as a result of flavorings and other materials. However, using tableting processes to mask tastes requires extensive use of flavors and is minimally successful relative to very negative tasting compounds.

Accordingly, there is a need for a drug delivery system that is capable of providing taste masking qualities and preserving controlled release characteristics. It is further desirable that such a drug delivery system be provided in a form that is both chewable and palatable to the animal.

SUMMARY OF THE INVENTION

By means of the instant invention there is provided a method for producing a drug delivery system for transporting pharmaceuticals in a chewable and palatable form for ingestion by an animal that provides taste masking properties to minimize the subject animal's ability to detect the drug's presence, and which also preserves the intended controlled release characteristics of the drug active. The delivery system produced by this method comprises a lipid source in which drug actives and other particles are homogeneously suspended to form a high solids suspension which can be solidified and molded into an oral dosage form, such as a pill or tablet, for swallowing and/or chewing. The lipid source is hydrophobic (lipophilic) and provides an external phase comprising the carrier for the suspension and also provides a hydrophobic film which continuously coats the hydrophilic drug actives and other materials. The lipid source can be comprised of petroleum based and/or food based lipophilic materials such as petroleum wax, vegetable or animal stearines or a high solids sharp melting point vegetable fat. The lipid source can consist of a single source "hard butter", which refers to a lipid system that has characteristics and/or a solid fat melting index similar to cocoa butter, and is similar in meltdown characteristics. The lipid source is selected to have a melting range of between 90°–160° F. that allows a sufficiently high melting point such that the final product will not melt while in transport or storage. The lipid system could also consist of combinations of hard butters and stearines in order to ensure a high melting point along with rapid meltdown. The melting point of the lipid may also be selected based upon the chewing texture preferences of the subject recipient. A melting point in the 90° range, for instance, will allow for melting in the mouth, which is preferable for humans, who may have an aversion to the waxy texture of a higher melting point lipid.

To prepare the suspension, the lipids are melted to the appropriate temperature, ranging from approximately 100° F. to 160° F. depending on the melting point. A surfactant, such as lecithen, is added to the melted lipid mixture to ensure optimum coating of hydrophilic particles comprising drug actives and other materials to be added later. Prior to being mixed in with the melted lipid base, the hydrophilic particles are first separately micro-encapsulated using standard pharmaceutical coating techniques. The type of encapsulation produced can vary depending on whether taste masking is desired or controlled released characteristics are desired, or both. After the hydrophilic particles are thusly prepared and encapsulated, they are added and mixed into the melted lipid base where a continuous phase lipid coating will take place within the lipid base. Care must be taken in the rate of addition of the solid particles within the suspension to avoid an emulsion and the creation of fatty granules. When made correctly there should be no detection of the granular nature of the solids added. The suspension should become homogeneous and give a consistent surface appearance of hard butter. Optionally, drug actives and other materials can be added to the melted lipid base without being pre-encapsulated. Frequently, the drug active is intended for immediate release effects, which might be hindered by excessive encapsulation. Other contemplated hydrophilic particles intended for suspension within the melted lipid base would include disruptive agents for blowing out the drug active particles from their encapsulation for rapid disintegration of the product. One type of such blowing agent comprises a starch based material, such as sodium starch glycolate, that will expand in the presence of moisture thus bursting the lipid encapsulation apart.

Once the solid particles are fully dispersed and suspended within the lipid base, the material is cooled down to slightly above the solidification point of the lipid base. The cooled material is poured into various molds for production into a final dosage form. The molds can comprise various configurations to create a multitude of desired shapes of the final product. Designs and other identifying indicia can be placed on the finished product at this stage as well. Because the suspension is capable of being molded into various shapes, the product lends itself to various creative delivery themes. By incorporating flavors into the molded product, certain food types can be imitated. For instance, cheese flavorings could be added to cube shapes, or meat flavoring could be added to bone shapes. Once the product is formed and properly cooled, it is then packaged and can be placed in storage.

The high solids suspension created by the method of this invention produces a chewable product for delivering intact pharmaceutical actives upon ingestion by the subject recipient such that taste masking and controlled release characteristics are preserved. When chewed, the molded suspension will break apart between, rather than through, the suspended particles, thus minimizing or eliminating the actual crushing of the encapsulation surrounding the particles. Because of the ability to suspend a significant amount of material within the high solid suspension itself, appropriate mixing will insure very acceptable content uniformity. Further, because the initial suspension is comprised of lipophilic material, which is then used to suspend the other materials, i.e., drug actives, pellets, disrupting agents, etc., flavorings need only be used to a level that is required for the resultant lower percentage lipophilic phase. This results in a very high flavoring effect with only the necessity of flavoring 20%–40% of the formula, as opposed to the entire mass.

DETAILED DESCRIPTION OF THE INVENTION

The method for producing the high solids suspension drug delivery system of the present invention essentially involves the combination of three processes: 1.) pre-encapsulation of active pharmaceutical ingredients, 2.) compounding of the liquid suspension comprising the lipid source in which dry solids are to be dispersed, and 3.) molding of the resultant liquid suspension into suitable dosage form.

In the pre-encapsulation stage, drug actives are prepared prior to being mixed in with the separately prepared melted lipid system. Basically, any drug may be prepared for use with the delivery system of this invention as long as it exists as a dry particle. The drug actives are pulverized to within a discrete particle size range of from about 10 microns to 300 microns. A smaller particle size will present a greater overall surface area of itself to be encapsulated, thus rendering the encapsulation effect of the drug active to be more efficient. The taste masking and, to some extent, the controlled release capabilities of the present invention depend on the effectiveness of encapsulation of the drug active. The hydrophobic nature of the encapsulating film retains the taste associated with the hydrophilic drug active. Encapsulation also prevents the early release of the drug to the animal's system. A solvent system containing a filming agent is mixed with the drug particles and blended at slow speed in a planetary mixer. The solvent can be water or ethanol; the filming agent may be ethylcellulose such as that marketed under the trademark Ethocel®. The filming agent, being hydrophobic, surrounds and coats the hydrophilic drug particles, forming micelles. The filming agent solvent solution is slowly added to the drug particles so that enough individual particles will adhere together to form larger granules having a size of approximately 300–500 microns. The degree of encapsulation can vary depending upon the number of layers of filming agent solvent solution applied. For taste masking purposes, however, extensive coating is not required. The film coating will have a thickness of about 1 micron or less. There exist various standard pharmaceutical coating techniques that are suitable for use with this invention, depending on the filming agent, type of active ingredient that is to be coated, and the drug release objective, such as immediate release vs. sustained release. Prior to granulation with the filming agent solvent solution, the active drug particles may be blended with a disrupting agent. The disrupting agent is formed of dry material particles which are also hydrophilic, facilitating the granulation that occurs during the encapsulation process. It is capable of rupturing the encapsulation so that immediate release of the drug active upon ingestion by the animal can be achieved. One such type of disrupting agent may comprise a sodium starch glycolate marketed under the trademark Explotab® This material will expand in the presence of moisture and will therefore burst the encapsulation surrounding it. Water is naturally present in gastrointestinal fluids and is able to pass by osmosis through the semi-permeable membrane of the film covering the particles. The water thus causes the starch to expand rapidly, blowing out the active particle from its encapsulation. Inner layers of encapsulation are thus exposed to moisture with each successive outer layer being burst, leading to a chain reaction and relatively rapid disintegration of the product.

The granulated blend of drug active particles is then dried to remove the solvent solution. The material may be tray dried or continuous dried in a floating bed type of device. The dried material is then screened between a 40 to 60 mesh screen to ensure particle size of 200 to 500 microns. The dried material can be stored for later use or may be blended with yet other dry materials, i.e., other drug actives, excipients, etc., in preparation for the compounding phase, in which the materials are enveloped by a continuous lipid coating within the lipid suspension.

Compounding is the process for dispersing dry solids formed into discrete particles, usually hydroscopic in nature, into a liquid system primarily comprised of lipids by which the dry solids are coated. It is this process that creates the carrier vehicle to transport the drug and for other desired materials which are also formed into discrete particles. The source of lipids can consist of a single component "hard butter", which refers to a lipid system that has characteristics and/or a solid fat melting index similar to cocoa butter and is similar in rapid meltdown characteristics. Typical lipids include, but are not limited to, partially hydrogenated vegetable oil, soybean oil, cottonseed oil, palm oil and palm oil and palm kernel oil. The lipid system could also consist of petroleum wax, vegetable or animal stearines, or a high solids sharp melting point vegetable fat, or also combinations of hard butters and stearines in order to achieve a high melting point along with the rapid meltdown. Rapid meltdown also relates to rapid solidification, which is critical in the molding process to avoid the separation of solids in suspension from the liquid compound medium. It is also possible to use mineral oil or petrolatum as the liquid hydrophobic system. The lipid source is melted to the appropriate temperature, which can range from approximately 90° F. to 160° F. The lipid should not be allowed to get too hot or it will lose its lubricity. A surfactant, such as lecithen, is added to insure optimum coating of the hydrophilic solid materials that are to be introduced into the melted lipid system. Optimally, the lethicen should be present in a concentration in a range between 0.5 to 1.0% of the melted lipid system. Other types of surfactants may also be utilized as long as they have a low hydrophilic to lipophilic balance (HLB) ratio, preferably between 1 to 3. Surfactants falling within this HLB ratio should be present in a concentration in a range between 0.5 to 25% of the melted lipid system. Typical surfactants include, but are not limited to, acetylated monoglyceriedes, alkyl aryl sulfonate, glycerol monostearate, oleic acid, poly oxyethylene lauric acid, and sodium oleate. Once the lipid source has been melted and the surfactant added in, the dry hydrophilic ingredients are slowly added in for coating. The dry ingredients comprise the granulated encapsulated material prepared separately, and also other non-encapsulated material as discussed above. The lipid system is able to receive a significant amount of dry material such that the resultant suspension may comprise 20–40% by weight lipophilic material, trapping 60–80% by weight dry hydrophilic material. The suspended particles can range from a fraction of a percent of any particular particle type up to 80% by weight, with the total of all particles not exceeding 80% by weight of the entire suspension. However, in order to successfully achieve the viscosity characteristics desired for the suspension, the actual lipid phase cannot exceed 40% of the compound base by weight. Likewise, the lipid phase cannot be less than 20% of the compound base by weight to achieve psuedoplasticity. It is important to maintain a continuous coating of the dry particles by the lipid system, yet not to such an extent that the desired Theological characteristics of the suspension is lost. If the lipid is present at less than 20% by weight of the suspension, the lipid coating will be too thin and will not exist in a continuous film. Thus, the compound will appear as a powder. If the lipid is present at greater than 40% by weight of the suspension, the desired psuedoplastic or thixotropic effect will not be achieved. Instead, an oily suspension of granules will result. The size of the particle selected for suspension is also critical. The key to obtaining the desired rheological properties is to be enable the lipid phase to stretch or exhibit polymeric properties. With a sufficiently small particle size, ideally 10–300 microns, a large surface area exists over which the lipid film must stretch. This results in a continuous lipid film that essentially functions as a semi-permeable membrane with a surface thickness of approximately two microns. Although the thickness of the film on the surface of the particles is extremely thin, it is nonetheless continuous and intact. Therefore the whole system acts as a lipid material, which will inhibit rapid dissolution in an aqueous system, while still providing a semi-permeable mechanism for release of the drug active. The system is applicable essentially to dry materials that are water-soluble. Highly oil-soluble materials would tend to be locked up in the film phase. Accordingly, drug actives that are lipophilic would not be suitable for the drug delivery system of this invention, at least for taste-masking purposes. The dry material must be added slowly, as the improper addition of these solid materials will cause the compounded material to flip as if it were an emulsion, with the end result being a non-continuous system that fails to achieve the desired rheological characteristics. If made correctly, there should be no detection in the finished product of the granular nature of the solids added. It is critical when mixing, that the lipid phase have the ability to stretch and exhibit polymeric properties. The dry solids are added slowly to insure continuous filming and coating. Improper processing will result in a mix of oil and particles, but the particles will not be coated with the lipid film and the desired pseudoplastic/thixotropic properties will not be obtained. The compounded materials will thicken with time and begin to take on the rheological properties required for this system. The suspension will become pseudoplastic allowing for easy forming, but being resistant to running or dripping unless shear is applied. The product will be homogeneous, having a surface appearance of the hard butter, or lipid, since the lipid is always on the outside of the dry materials as a continuous microfilm. The addition of the dry materials to the lipid system under this process could take between 30 minutes up to one hour; the timing is generally the same, regardless of the quantity of the suspension to be compounded. The dry materials are best added incrementally, with two to four percent by weight of the total formula weight being added in to the lipid system at two to three minute intervals. The time may vary with the size of the particle. It is a slow process, and each particle must be dispersed within the lipid system. The compound is mixed using appropriate means known to those skilled in the art, such as a planetary mixer, swept surface mixer or a recirculating system. Low to medium shear should be applied and should be kept below 1,000 rpms. High shear should be avoided as it creates too much friction, which can lead to decreased lubricity of the lipid that will adversely affect its ability to form a continuous film. The various dry solid materials can be compounded into the suspension up to 50% by volume, with weight not being a factor. As a result, depending on the density of the suspended solids, the weight of the suspended solids within the high solid suspension could be 2–3 times the actual weight of the lipid it is suspended into while still maintaining the desired psuedoplastic characteristics. The high solids suspension is not limited by the density of the suspended particles.

Once the dry solid material is fully dispersed, the suspension is then cooled down to a temperature within a degree or two above whatever the solidification of the lipid base medium is. The suspension may optionally be put through a process called tempering, which is a process of raising and lowering the temperature just above and below the solidification point. This ensures formation of optimum lipid crystal structures; lipids form polymorphic crystals, which eventually turn into optimum stable crystals. The objective is to form the optimum stable crystals quickly or use a lipid system that is self tempering. Once the suspension is properly cooled and tempered it is pumped and metered into an appropriate mold where it is cooled at temperatures 10° to 40° F. below the solidification point of its lipophilic medium. This will result in a slight shrinkage because of the increased densification of the lipophilic phase once it turns into crystalline material. The shrinkage allows for rapid release from the mold. The finished product can be provided in various dosage forms and shapes depending upon the configuration of the mold. Various other designs or indicia may be placed on the product, such as product name, numbers, drawings, etc. Once formed, the product is packaged and prepared for storage. It is also possible to mold the product in large blocks for storage. These blocks can be melted down at a later time for appropriate dosage molding.

Alternatively, the liquid suspension could be super cooled below the actual crystallization point of the lipophilic material through a heat exchanger and then sheeted in a semi-soft format. It is then dropped through forming rolls containing the design or configuration that would emboss the final desired shape on the super-cooled sheet. Once this sheet leaves the embossing rolls, cool air will set it rapidly.

EXAMPLES

The following examples show ingredients and concentrations thereof for preparing various veterinary products comprising the drug delivery system of the instant invention. For each example, Table A shows the formulation for preparing the pre-encapsulated drug active. Table B shows the formulation for compounding the lipid base and dry materials for preparing the high solids suspension. While the examples herein are for specific drugs, it is to be understood that the preparation methods are applicable for any type of drug, whether for animal or human use. The range of drugs that can be carried in the system is very wide, and can comprise analgenics, anti-inflammatory agents, gastrointestinal medications, hormone products, cardiovascular preparations and immunoglobulins to name a few. Many other types of drugs and products can also be carried as will be understood by those skilled in the art.

Example I

TABLE A

Encapsulation of Drug Active
Carprofen Granulation
BATCH FORMULA

| Ingredient | Weight (grams) | % |
|---|---|---|
| Carprofen (Drug Active) | 7.580 | 18.95% |
| Ethocel ® (30 gm of 4% solution) | 1.200 | 3.00% |
| Explotab ® | 31.220 | 78.05% |
| Totals | 40 | 100.00% |

TABLE B

Compounding of Product
Carprofen 100 mg Dose in a 1.8 gm Pill
BATCH FORMULA

| Ingredient | Weight (grams) | % |
|---|---|---|
| kaomel (lipid) | 0.4536 | 25.20% |
| duratex (lipid) | 0.1944 | 10.80% |
| lecithin (surfactant) | 0.0108 | 0.60% |
| chedlong #1 (flavoring) | 0.2430 | 13.50% |
| cheese flavor 2517 (flavoring) | 0.0090 | 0.50% |
| cheese flavor 1200s (flavoring) | 0.0270 | 1.50% |
| salt | 0.0180 | 1.00% |

TABLE B-continued

Compounding of Product
Carprofen 100 mg Dose in a 1.8 gm Pill
BATCH FORMULA

| Ingredient | Weight (grams) | % |
|---|---|---|
| whey | 0.2642 | 14.68% |
| carprofen granulation (drug active) | 0.5800 | 32.22% |
| (From table A) | | |
| Totals | 1.8 | 100.00% |

Example II

TABLE A

Encapsulation of Drug Active
Enalapril Granulation
BATCH FORMULA

| Ingredient | Weight (grams) | % |
|---|---|---|
| Enalapril Maleate (Drug Active) | 1.460 | 3.65% |
| Ethocel ® (20 gm of 4% solution) | 0.800 | 2.00% |
| Explotab ® | 37.740 | 94.35% |
| Totals | 40 | 100.00% |

TABLE B

Compounding of Product
Enapril 5 mg Dose in a 1.5 gm Pill
BATCH FORMULA

| Ingredient | Weight (grams) | % |
|---|---|---|
| kaomel (lipid) | 0.3780 | 25.20% |
| duratex (lipid) | 0.1620 | 10.80% |
| Explotab ® | 0.2535 | 16.90% |
| lecithin (surfactant) | 0.0090 | 0.60% |
| chedlong #1 (flavoring) | 0.2025 | 13.50% |
| cheese flavor 2517 (flavoring) | 0.0075 | 0.50% |
| cheese flavor 1200s (flavoring) | 0.0225 | 1.50% |
| salt | 0.0150 | 1.00% |
| whey | 0.3000 | 20.00% |
| enapril granulation (drug active) | 0.1500 | 10.00% |
| (From Table A) | | |
| Totals | 1.5 | 100.00% |

Example III

TABLE A

Encapsulation of Drug Active
Furosemide Granulation
BATCH FORMULA

| Ingredient | Weight (grams) | % |
|---|---|---|
| Furosemide (Drug Active) | 3.66 | 9.15% |
| Ethocel ® (20 gm of 4% solution) | 0.80 | 2.00% |
| Explotab ® | 35.54 | 88.85% |
| Totals | 40 | 100.00% |

TABLE B

Compounding of Product
Furosemide 12.5 mg Dose in a 1.5 gm Pill
BATCH FORMULA

| Ingredient | Weight (grams) | % |
|---|---|---|
| kaomel (lipid) | 0.3780 | 25.20% |
| duratex (lipid) | 0.1620 | 10.80% |
| Explotab ® | 0.2535 | 16.90% |
| lecithin (surfactant) | 0.0090 | 0.60% |
| chedlong #1 (flavoring) | 0.2025 | 13.50% |
| cheese flavor 2517 (flavoring) | 0.0075 | 0.50% |
| cheese flavor 1200s (flavoring) | 0.0225 | 1.50% |
| salt | 0.0150 | 1.00% |
| whey | 0.3000 | 20.00% |
| furosemide granulation (drug active) | 0.1500 | 10.00% |
| (From Table A) | | |
| Totals | 1.5 | 100.00% |

Example IV

TABLE A

Encapsulation of Drug Active
Levothyroxine Granulation
BATCH FORMULA

| Ingredient | Weight (grams) | % |
|---|---|---|
| Levothyroxine Sodium (Drug Active) | 0.120 | 0.30% |
| Ethocel ® 20 gm of 4% solution) | 0.800 | 2.00% |
| Explotab ® | 39.080 | 97.70% |
| Totals | 40 | 100.00% |

TABLE B

Compounding of Product
Levothyroxine 0.4 mg Dose in a 1.5 gm Pill
BATCH FORMULA

| Ingredient | Weight (grams) | % |
|---|---|---|
| kaomel (lipid) | 0.3780 | 25.20% |
| duratex (lipid) | 0.1620 | 10.80% |
| Explotab ® | 0.2535 | 16.90% |
| lecithin (surfactant) | 0.0090 | 0.60% |
| chedlong #1 (flavoring) | 0.2025 | 13.50% |
| cheese flavor 2517 (flavoring) | 0.0075 | 0.50% |
| cheese flavor 1200s (flavoring) | 0.0225 | 1.50% |
| salt | 0.0150 | 1.00% |
| whey | 0.3000 | 20.00% |
| levothyroxine granulation (drug active) | 0.1500 | 10.00% |
| (From Table A) | | |
| Totals | 1.5 | 100.00% |

Example V

TABLE A

Encapsulation of Drug Active
Prednisolone Granulation
BATCH FORMULA

| Ingredient | Weight (grams) | % |
|---|---|---|
| Prednisolone (Drug Active) | 1.460 | 3.65% |
| Ethocel ® (20 gm of 4% solution) | 0.800 | 2.00% |
| Explotab ® | 37.740 | 94.35% |
| Totals | 40 | 100.00% |

TABLE B

Compounding of Product
Prednisolone 5 mg Dose in a 1.5 gm Pill
BATCH FORMULA

| Ingredient | Weight (grams) | % |
|---|---|---|
| kaomel (lipid) | 0.3780 | 25.20% |
| duratex (lipid) | 0.1620 | 10.80% |
| Explotab ® | 0.2535 | 16.90% |
| lecithin (surfactant) | 0.0090 | 0.60% |
| chedlong #1 (flavoring) | 0.2025 | 13.50% |
| cheese flavor 2517 (flavoring) | 0.0075 | 0.50% |
| cheese flavor 1200s (flavoring) | 0.0225 | 1.50% |
| salt | 0.0150 | 1.00% |
| whey | 0.3000 | 20.00% |
| prednisolone granulation (drug active) | 0.1500 | 10.00% |
| (From Table A) | | |
| Totals | 1.5 | 100.00% |

Process Example
(Process Utilized for Previous Formulation Examples)
Granulation and Micro-Encapsulation
1. Blend drug active particles with Explotab® (sodium starch glycolate) in a 5 qt. planetary mixer.
2. Granulate with 4% Ethocel® filming agent solution (Ethocel® and ethanol) by slowly adding a small stream of solution to the dry mix while mixing at slow speed.
3. Allow granulated material to tray dry until solvent is removed.
4. Screen through #40 mesh screen to ensure particle size of between 200–500 microns.

Compounding
1. Melt duratex (vegetable stearines) in jacketed mixing bowl (140°–150° F.)
2. Add, melt and blend Kaomel (98° vegetable hard butter)
3. Add and blend lecithin (may be able to reduce heat to 135° F.)
4. Screen (40 mesh) and blend all dry ingredients
   Chedlong #1 (dried cheese solids)
   Cheese Flavor 2517
   Cheese Flavor 1200S
   Salt
   Whey
   Active Granulation
   Explotab® (sodium starch glycolate)
5. Slowly add dry blend in incremental amounts every few minutes to melted fats (with stirring) and stir until smooth with no lumps (approximately 1 hour). Maintain mixing and lower temperature 135° (tempering) then mold.
6. Cool at 70° F. until compound solidifies and shrinks. Then flip mold to remove individual doses; identification coded by reverse embossing within each mold.

The method of this invention, therefore, allows for the delivery of pharmaceuticals in a solid delivery system that preserves the taste masking and controlled release characteristics that have been imparted to the pharmaceuticals through microencapsulation prior to compounding into the high solids suspension. The product thus prepared allows for a more effective delivery of required dosages and a more predictable controlled rate of delivery. The pseudoplastic nature of the high solids suspension allows it to become a carrier of other materials as well, thus creating more options with respect to which type of drugs are to be delivered orally and also with respect to their rate of release within the animals' system. Uncoated time release pellets and other excipients are readily compounded into the lipid system. Therefore, because there is no damage during molding procedures, the timing of release considerations of any drug are not restricted. The intact delivery of the drug actives allows for greater predictability of time release and greater certainty of ingestion by the subject recipients.

The high solids suspension is very versatile and presents a number of options in selecting a final delivery form. Because the products formed from the high solids suspension are intended for both animal and human use, different considerations come into play when preparing the product for the respective recipient. With respect to selection of the lipid base, chewing texture characteristics may be important. Humans may have an aversion to waxy textured chewable products and would generally prefer a melt-in-the-mouth sensation. Accordingly, a lipid having a melting range from about 90° to 100° F. would be used as the lipid source when preparing products for human consumption. Animals generally have no objection to a waxy tasting substance, so a higher melting point lipid may be used when preparing products for animal consumption. Taste masking is more readily accomplished with the high solids suspension because the suspending base is comprised of lipophilic material that envelopes other hydrophilic materials, i.e., drug actives, pellets, disrupting agents, etc. Flavorings thus need only be used to a level that is required for the resultant lower percentage lipophilic phase. This results in a very high flavoring effect with only the necessity of flavoring the 20%–40% lipophilic portion of the formula, as opposed to the entire mass. Lipophilic flavors can often be superior as masking media because of their solubility compared to water-soluble flavors. By incorporating flavors into the molded product, certain food types can be imitated. For instance, cheese flavorings could be added to cube shapes, or meat flavoring could be added to bone shapes.

The high solids suspension created by the method of this invention produces a chewable product for delivering intact pharmaceutical actives upon ingestion by the subject recipient such that the encapsulation which affects the taste masking and controlled release characteristics of the drug is preserved due to the formation of the lipid crystalline structure in which the particles are suspended. When chewed, the molded suspension will break apart along cleavage lines of the crystalline structure, and will break apart between, rather than through, the suspended particles, thus minimizing or eliminating the actual crushing of the encapsulation surrounding the particles. Heat in the subject recipient's mouth, as well as friction and pressure generated by chewing, melt the crystalline structure. This liquefies the material for ease of swallowing, but does not itself affect the rapid release of active.

The density of the product, which can be manipulated to have a specific gravity in the range between 1.1 to 2.0, provides additional options for targeting the delivery of the carried drug. Advantage can be made of the animal recipient's anatomy for purposes of controlled release and for avoidance of premature passage of the drug through the animal's digestive system. The high density of the product causes the digested material to physically drop to the bottom of the animal's stomach where it will remain until substantially dissolved. Having a much greater density than water, the material will have a resistance to being swept along with other digested material. The drug, therefore, will be able to remain in place until its entire dosage is effectively delivered. Accordingly, the ability to control the density of the suspension enables increased effectiveness in the target delivery of drugs. As an alternative to a chewable form the product may be delivered to the animal in the form of a bolus, which would be intended for swallowing whole. This form may be desired for sustained release delivery situations.

Various changes and modifications may be made within this invention as will be apparent to those skilled in the art. Such changes and modifications are within the scope and teaching of this invention as defined in the claims appended hereto.

What is claimed is:

1. A method for preparing a drug delivery system for transporting drug active particles for ingestion by a subject recipient, said delivery system comprising a suspension comprising a lipid source in which said particles and other dry solids are homogeneously suspended, said method comprising the steps of:

microencapsulating said drug particles by granulating with a filming agent, melting said lipid source to a liquid state, adding a surfactant to said melted lipid source to enhance coating of said lipid source, mixing said dry solids and said microencapsulated drug particles within said melted liquid lipid source until said suspension is formed such that said dry solids and said microencapsulated drug particles are continuously coated by said lipid source such that said suspension exhibits pseudoplastic and/or thixotropic properties, and molding said suspension into an oral dosage form for swallowing or chewing.

2. The method of claim 1 in which said drug particles are formed into granules having a particle size of between 200 to 500 microns.

3. The method of claim 1 in which said drug particles include a rupturing agent capable of rupturing said microencapsulation.

4. The method of claim 3 in which said rupturing agent is sodium starch glycolate.

5. The method of claim 1 in which said lipid source forms 20% to 40% by weight of said suspension, and said drug particles and said dry solids collectively form 60% to 80% by weight of said suspension.

6. The method of claim 5 in which said drug particles and said dry solids comprise a plurality of types of ingredients, any one of said types of ingredients being present in a range from a fraction of a percent to 80% by weight of said suspension.

7. The method of claim 5 in which said drug particles and dry solids are added in an amount sufficient to give said suspension a specific gravity in a range between 1.1 to 2.0.

8. The method of claim 5 in which said dry solids have a size ranging from 10 to 300 microns in diameter.

9. The method of claim 5 in which said dry solids are added to said melted liquid lipid source at a rate of two to four per cent dry solids of a total formula weight of said suspension per two minute interval.

10. The method of claim 1 in which said lipid source consists of a hard butter, petroleum wax, vegetable fat or animal stearines.

11. The method of claim 1 in which said suspension contains a rupturing agent capable of releasing said drug particles and said dry solids from said lipid coating after ingestion by said subject recipient.

12. The method of claim 11 in which said rupturing agent is sodium starch glycolate.

13. The method of claim 1 in which lipophilic artificial flavorings are added to said suspension in an amount dependent upon a percentage by weight of lipids present in said suspension.

14. The method of claim 1 in which said oral dosage form is selected which comprises and imitates a natural food source shape.

* * * * *